US012602782B2

(12) United States Patent
Iwadate

(10) Patent No.: US 12,602,782 B2
(45) Date of Patent: Apr. 14, 2026

(54) IMAGE PROCESSING DEVICE, IMAGE PROCESSING METHOD, AND STORAGE MEDIUM

(71) Applicant: NEC Corporation, Tokyo (JP)

(72) Inventor: Yuji Iwadate, Tokyo (JP)

(73) Assignee: NEC CORPORATION, Tokyo (JP)

( * ) Notice: Subject to any disclaimer, the term of this patent is extended or adjusted under 35 U.S.C. 154(b) by 294 days.

(21) Appl. No.: 18/409,907

(22) Filed: Jan. 11, 2024

(65) Prior Publication Data

US 2024/0212142 A1 Jun. 27, 2024

Related U.S. Application Data

(63) Continuation of application No. 18/574,123, filed as application No. PCT/JP2023/031837 on Aug. 31, 2023.

(30) Foreign Application Priority Data

Dec. 27, 2022 (WO) ................. PCT/JP2022/048310

(51) Int. Cl.
*G06K 9/00* (2022.01)
*G06T 7/00* (2017.01)
*G16H 50/20* (2018.01)

(52) U.S. Cl.
CPC ........... *G06T 7/0012* (2013.01); *G16H 50/20* (2018.01); *G06T 2207/10068* (2013.01); *G06T 2207/30096* (2013.01)

(58) Field of Classification Search
CPC ......... G06T 7/0012; G06T 2207/10068; G06T 2207/30096; G06T 7/00; G16H 50/20
See application file for complete search history.

(56) References Cited

U.S. PATENT DOCUMENTS 11,024,031 B1 6/2021 Nozaki et al.
12,106,473 B2 * 10/2024 Wang .................... A61B 5/425
(Continued)

FOREIGN PATENT DOCUMENTS

CN 110136103 A * 8/2019 .......... G06T 7/0012
CN 110163195 A * 8/2019 .............. G06T 7/40
(Continued)

OTHER PUBLICATIONS

International Search Report for PCT Application No. PCT/JP2023/031837, mailed on Dec. 27, 2022.
(Continued)

*Primary Examiner* — Xin Jia
(74) *Attorney, Agent, or Firm* — Sughrue Mion, PLLC

(57) ABSTRACT

The image processing device 1X includes a first acquisition means 30X, a second acquisition means 31X, and an inference means 33X. The first acquisition means 30X acquires a set value of a first index indicating an accuracy relating to a lesion analysis. The second acquisition means 31X acquires, for each of plural models which make inference regarding a lesion, a predicted value of a second index, which is an index of the accuracy other than the first index, on an assumption that the set value of the first index is satisfied. The inference means 33X makes inference regarding the lesion included in an endoscopic image of an examination target, based on the predicted value of the second index and the plural models.

16 Claims, 12 Drawing Sheets

(56)  References Cited

U.S. PATENT DOCUMENTS

| | | | |
|---|---|---|---|
| 2012/0316421 A1 | 12/2012 | Kumar et al. | |
| 2015/0254411 A1 | 9/2015 | Ono et al. | |
| 2016/0345834 A1 | 12/2016 | Hasan et al. | |
| 2018/0216197 A1 | 8/2018 | Davicioni et al. | |
| 2018/0247107 A1 | 8/2018 | Murthy et al. | |
| 2018/0253839 A1 | 9/2018 | Zur | |
| 2019/0085406 A1 | 3/2019 | Mortimer et al. | |
| 2020/0279368 A1* | 9/2020 | Tada .................. | A61B 1/00016 |
| 2020/0395123 A1 | 12/2020 | Akselrod-Ballin et al. | |
| 2021/0090694 A1 | 3/2021 | Colley et al. | |
| 2021/0249136 A1 | 8/2021 | Reagan et al. | |
| 2021/0374953 A1 | 12/2021 | Asiedu et al. | |
| 2022/0025469 A1 | 1/2022 | Mortimer et al. | |
| 2022/0138932 A1 | 5/2022 | Bonakdar Sakhi et al. | |

FOREIGN PATENT DOCUMENTS

| | | | |
|---|---|---|---|
| WO | 2018/225448 A1 | 12/2018 | |
| WO | 2019/146077 | 8/2019 | |

OTHER PUBLICATIONS

US Office Action for U.S. Appl. No. 18/409,893, mailed on Dec. 1, 2025.

M Shahbaz Ayyaz et al. "Hybrid Deep Learning Model for Endoscopic Lesion Detection and Classification Using Endoscopy Videos" Diagnostics, pub. Dec. 25, 2021. (Year: 2021).

US Office Action for U.S. Appl. No. 18/574,123, mailed on Dec. 8, 2025.

* cited by examiner

<u>100</u>:ENDOSCOPIC EXAMINATION SYSTEM

FIRST INDEX (THE HIGHER, THE BETTER)

G1  G2

G3

P13

P12

P11

SET
VALUE
Vs1

FIRST MODEL

SECOND MODEL

THIRD MODEL

PREDICTED
VALUE Vp13

PREDICTED
VALUE Vp11

PREDICTED
VALUE Vp12

SECOND INDEX (THE LOWER, THE BETTER)

FIRST INDEX (THE HIGHER, THE BETTER)

SET
VALUE
Vs2

P21   G1   P22   G2

P23

G3

FIRST MODEL

SECOND MODEL

THIRD MODEL

PREDICTED
VALUE Vp21

PREDICTED
VALUE Vp22

PREDICTED
VALUE Vp23

SECOND INDEX (THE LOWER, THE BETTER)

1

IMAGE PROCESSING DEVICE, IMAGE PROCESSING METHOD, AND STORAGE MEDIUM

This application is a Continuation of U.S. application Ser. No. 18/574,123 filed on Dec. 26, 2023, which is a National Stage Entry of PCT/JP2023/031837 filed on Aug. 31, 2023, which claims priority from PCT International Application PCT/JP2022/048310 filed on Dec. 27, 2022, the contents of all of which are incorporated herein by reference, in their entirety.

TECHNICAL FIELD

The present disclosure relates to a technical field of an image processing device, an image processing method, and a storage medium for processing an image to be acquired in endoscopic examination.

BACKGROUND

There is proposed an endoscopic examination system which supports the diagnosis of the endoscopic examination. For example, Patent Literature 1 discloses a diagnosis support system for generating a plurality of detection results based on a plurality of identification engine candidates which output different detection results from each other when detecting an attention area from an inputted image.

CITATION LIST

Patent Literature

Patent Literature 1: WO2019/146077

SUMMARY

Problem to be Solved

In the system which autonomously detects a lesion using an endoscopic image acquired in the endoscopic examination, requirements for respective indices (e.g., sensitivity, specificity, and the like) of the accuracy of the lesion detection vary depending on the user.

In view of the above-described issue, it is therefore an example object of the present disclosure to provide an image processing device, an image processing method, and a storage medium capable of suitably detecting a lesion in an endoscope examination.

Means for Solving the Problem

One mode of the image processing device is an image processing device including:
a first acquisition means configured to acquire a set value of a first index indicating an accuracy relating to a lesion analysis;
a second acquisition means configured to acquire, for each of plural models which make inference regarding a lesion, a predicted value of a second index, which is an index of the accuracy other than the first index, on an assumption that the set value of the first index is satisfied; and
an inference means configured to make inference regarding the lesion included in an endoscopic image of an examination target, based on the predicted value of the second index and the plural models.

One mode of the image processing method is an image processing method executed by a computer, the image processing method including:
acquiring a set value of a first index indicating an accuracy relating to a lesion analysis;
acquiring, for each of plural models which make inference regarding a lesion, a predicted value of a second index, which is an index of the accuracy other than the first index, on an assumption that the set value of the first index is satisfied; and
making inference regarding the lesion included in an endoscopic image of an examination target, based on the predicted value of the second index and the plural models.

One mode of the storage medium is a storage medium storing a program executed by a computer, the program causing the computer to:
acquire a set value of a first index indicating an accuracy relating to a lesion analysis;
acquire, for each of plural models which make inference regarding a lesion, a predicted value of a second index, which is an index of the accuracy other than the first index, on an assumption that the set value of the first index is satisfied; and
make inference regarding the lesion included in an endoscopic image of an examination target, based on the predicted value of the second index and the plural models.

Effect

An example advantage according to the present invention is to suitably detect a lesion in an endoscope examination.

EXAMPLE EMBODIMENTS

Hereinafter, example embodiments of an image processing device, an image processing method, and a storage medium will be described with reference to the drawings.

First Example Embodiment

(1-1) System Configuration

Figure 1:
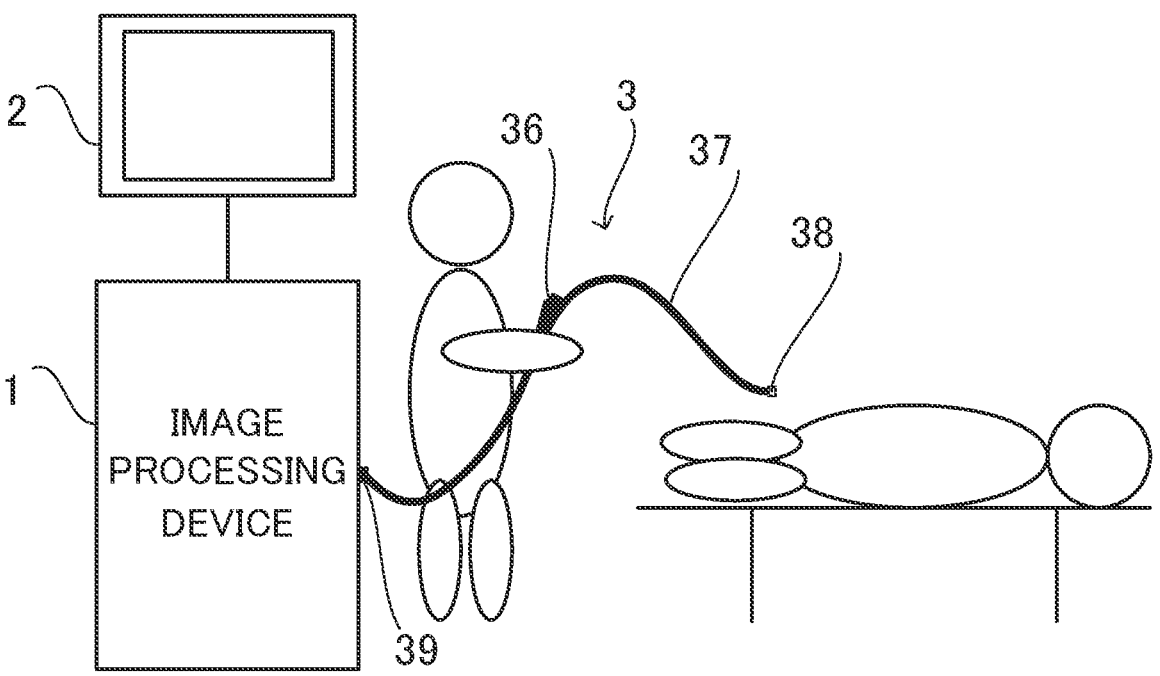
FIG. 1 It illustrates a schematic configuration of an endoscope examination system.

FIG. 1 shows a schematic configuration of an endoscopic examination system 100. As shown in FIG. 1, an endoscopic examination system 100 presents a region (also referred to as "lesion region") suspected of lesion on an image of an examination target to an examiner such as a doctor who conducts an examination or treatment using an endoscope. The endoscopic examination system 100 is mainly provided with an image processing device 1, a display device 2, and an endoscope 3 connected to the image processing device 1.

The image processing device 1 acquires an image (also referred to as "endoscopic image Ia") captured by the endoscope 3 in time series from the endoscope 3 and displays a screen image based on the endoscopic image Ia on the display device 2. The endoscopic image Ia is an image captured at predetermined time intervals in at least one of the insertion processes of the endoscope 3 to the subject and/or the ejection processes of the endoscope 3 from the subject. In the present example embodiment, the image processing device 1 analyzes the endoscopic image Ia regarding at least the existence of a lesion region and displays the information regarding the analysis result on the display device 2. Thus, the image processing device 1 can support a decision making by the examiner who is a doctor or the like, such as the determination of the way of manipulation of the endoscope and the determination of the treatment policy for the subject of the examination. Hereafter, the above-described analysis on the endoscopic image Ia is also referred to as "lesion analysis".

The display device 2 is a display or the like for display information based on the display signal supplied from the image processing device 1.

The endoscope 3 mainly includes an operation unit 36 for examiner to perform a predetermined input, a shaft 37 which has flexibility and which is inserted into the organ to be photographed of the subject, a tip unit 38 having a built-in photographing unit such as an ultra-small image pickup device, and a connecting unit 39 for connecting with the image processing device 1.

The configuration of the endoscopic examination system 100 shown in FIG. 1 is an example, and various change may be applied thereto. For example, the image processing device 1 may be configured integrally with the display device 2. In another example, the image processing device 1 may be configured by a plurality of devices.

It is noted that the target of the endoscopic examination in the present disclosure is not limited to a large bowel, it may be any organ subject to endoscopic examination such as esophagus, stomach, pancreas. Examples of the target of the endoscopic examination in the present disclosure include a laryngendoscope, a bronchoscope, an upper digestive tube endoscope, a duodenum endoscope, a small bowel endoscope, a large bowel endoscope, a capsule endoscope, a thoracoscope, a laparoscope, a cystoscope, a cholangioscope, an arthroscope, a spinal endoscope, a blood vessel endoscope, and an epidural endoscope. A disorder (also referred to as "target disorder") subjected to detection in the endoscopic examination are exemplified as (a) to (f) below.

(a) Head and neck: pharyngeal cancer, malignant lymphoma, papilloma (b) Esophagus: esophageal cancer, esophagitis, esophageal hiatal hernia, Barrett's esophagus, esophageal varices, esophageal achalasia, esophageal submucosal tumor, esophageal benign tumor (c) Stomach: gastric cancer, gastritis, gastric ulcer, gastric polyp, gastric tumor (d) Duodenum: duodenal cancer, duodenal ulcer, duodenitis, duodenal tumor, duodenal lymphoma (e) Small bowel: small bowel cancer, small bowel neoplastic disease, small bowel inflammatory disease, small bowel vascular disease (f) Large bowel: colorectal cancer, colorectal neoplastic disease, colorectal inflammatory disease; colorectal polyps, colorectal polyposis, Crohn's disease, colitis, intestinal tuberculosis, hemorrhoids.

(1-2) Hardware Configuration

Figure 2:
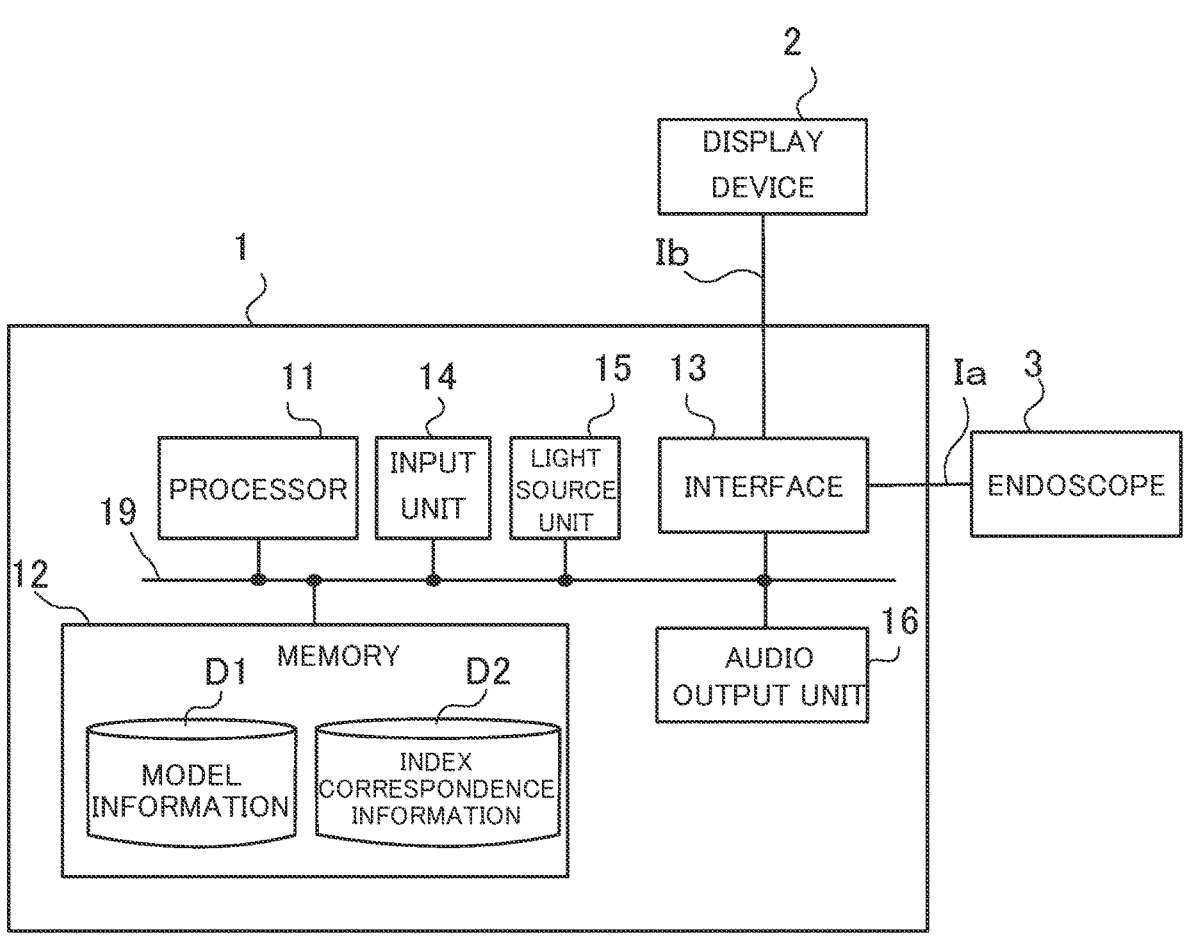
FIG. 2 It illustrates a hardware configuration of an image processing device.

FIG. 2 shows a hardware configuration of the image processing device 1. The image processing device 1 mainly includes a processor 11, a memory 12, an interface 13, an input unit 14, a light source unit 15, and an audio output unit 16. Each of these elements is connected via a data bus 19.

The processor 11 executes a predetermined process by executing a program or the like stored in the memory 12. The processor 11 is one or more processors such as a CPU (Central Processing Unit), a GPU (Graphics Processing Unit), and a TPU (Tensor Processing Unit). The processor 11 may be configured by a plurality of processors. The processor 11 is an example of a computer.

The memory 12 is configured by a variety of volatile memories which is used as working memories, and non-volatile memories which stores information necessary for the process to be executed by the image processing device 1, such as a RAM (Random Access Memory) and a ROM (Read Only Memory). The memory 12 may include an external storage device such as a hard disk connected to or built in to the image processing device 1, or may include a storage medium such as a removable flash memory. The memory 12 stores a program for the image processing device 1 to execute each process in the present example embodiment.

The memory 12 also stores model information D1 and index correspondence information D2, wherein the model information D1 is information regarding lesion analysis models, which are models to be used for lesion analysis in the endoscopic examination and the index correspondence information D2 indicates the correspondence between two different indices each indicating the degree of accuracy regarding the lesion analysis models. Examples of the indices indicating the degree of accuracy regarding the lesion analysis models include sensitivity (i.e., detection rate or true positive rate), specificity, false positive rate, and precision. The model information D1 and the index correspondence information D2 will be described later.

The interface 13 performs an interface operation between the image processing device 1 and an external device. For example, the interface 13 supplies the display information "Ib" generated by the processor 11 to the display device 2. Further, the interface 13 supplies the light generated by the light source unit 15 to the endoscope 3. The interface 13 also provides an electrical signal to the processor 11 indicative of the endoscopic image Ia supplied from the endoscope 3. The interface 13 may be a communication interface, such as a network adapter, for wired or wireless communication with the external device, or a hardware interface compliant with a USB (Universal Serial Bus), a SATA (Serial AT Attachment), or the like.

The input unit 14 generates an input signal based on the operation by the examiner. Examples of the input unit 14 include a button, a touch panel, a remote controller, and a voice input device. The light source unit 15 generates light for supplying to the pointed end unit 38 of the endoscope 3. The light source unit 15 may also incorporate a pump or the like for delivering water and air to be supplied to the endoscope 3. The audio output unit 16 outputs a sound under the control of the processor 11.

Next, the model information D1 and the index correspondence information D2 stored in the memory 12 will be described in detail.

The model data D1 includes parameters of a plurality of lesion analysis models that are candidates for use in the lesion analysis.

Here, each lesion analysis model is a model (engine) configured to output, in response to an input of an endoscopic image, the inference result regarding a lesion region in the inputted endoscopic image. Each lesion analysis model is, for example, a machine learning model (including a statistical model, hereinafter the same) having any architecture such as a neural network and a support vector machine. In this instance, each of the lesion analysis models is trained using training data, and parameters of each lesion analysis model obtained by training are stored in advance in the memory 12 as the model information D1. For example, the training data includes a plurality of records each of which is a set of an endoscopic image for input and correct answer data, wherein the correct answer data indicates the inference result to be outputted by each lesion analysis model when the endoscopic image is inputted thereto. The lesion analysis models may be models with different architectures from each other and may be models trained by different training datasets. Typical examples of the neural network used in the architecture of a lesion analysis model include Fully Convolutional Network, SegNet, U-Net, V-Net, Feature Pyramid Network, Mask R-CNN, and DeepLab. Then, if a lesion analysis model is configured by a neural network, the model information D1 includes various parameters (including hyperparameters) regarding the layer structure, the neuron structure of each layer, the number of filters and the filter size in each layer, and the weight for each element of each filter, for each lesion analysis model.

The lesion analysis model may be a lesion detection engine that detects the presence or absence of a lesion region in an inputted endoscopic image, or may be a classification engine that classifies the presence or absence of a lesion region in an endoscopic image, or may be a segmentation engine that segments an inputted endoscopic image into regions based on the presence or absence of a lesion region.

For example, if the lesion analysis model is a lesion detection engine, the lesion analysis model outputs an inference result indicating a bounding box indicating the existence range of the lesion region in an endoscopic image inputted thereto and the degree of confidence (i.e., confidence score) that the bounding box indicates the existence range of the lesion region, respectively. The confidence score is, for example, the degree of confidence for each class (here, there are two classes: presence of a lesion region and absence of a lesion region) outputted from the output layer of the neural network when a lesion analysis model is constituted by a neural network. It is hereinafter assumed that the higher the confidence score is, the greater the probability becomes.

In addition, if the lesion analysis model is a classification engine, the lesion analysis model outputs an inference result indicating, for example, the presence or absence of a lesion region in an endoscopic image inputted thereto and the confidence score (classification score) corresponding to each of the presence and absence of the lesion region, respectively. In addition, if the lesion analysis model is a segmentation engine, the lesion analysis model outputs an inference result indicating, for example, the presence or absence of a lesion region in pixel units (which may be block units configured by a plurality of pixels) in an endoscopic image inputted thereto and the confidence score, in pixel units, of the presence of the lesion region, respectively. The above-mentioned inference results outputted by the lesion analysis model are merely examples, and any type of an inference result may be outputted from the lesion analysis model.

Then, the presence or absence of a lesion region is finally determined based on the above-described inference result outputted by the lesion analysis model and a threshold value (also referred to as "threshold value for lesion determination") for determining whether or not there is a lesion region. For example, the threshold value for lesion determination is a threshold value that can be set by a user and, for example, is compared with the above-described confidence score. For example, when the lesion analysis model is a classification engine, the image processing device 1 determines that there is a lesion region when the confidence score corresponding to the class of the presence of the lesion region is equal to or more than the threshold value for lesion determination, and determines that there is no lesion region when the above-described confidence score is less than the threshold value for lesion determination. Even in the case where the lesion analysis model is a lesion detection engine, the image processing device 1 determines that there is a lesion region in the bounding box when the confidence score of the presence of the lesion region in the bounding box is equal to or larger than the threshold value for lesion determination while it determines that there is no lesion region in the bounding box when the above-described confidence score is less than the threshold value for lesion determination. Similarly, in the case where the lesion analysis model is the segmentation engine, the image processing device 1 determines the presence or absence of a lesion region in pixel units, based on the result of comparison between the confidence score of the presence of a lesion region in pixel units and the threshold value for lesion determination.

It is possible to adjust the sensitivity and the specificity of each lesion analysis model by adjusting the threshold value for lesion determination to be used in the each lesion analysis model. Further, the lesion analysis model may be a model that outputs the determination result of the presence or absence of a lesion region based on the threshold value for lesion determination. In this case, the threshold value for lesion determination is used as a hyperparameter of the lesion analysis model.

The index correspondence information D2 is information indicating the correspondence relation between two indices (referred to as "first index" and "second index", respectively) regarding the accuracy of each lesion analysis model. As will be described later, the first index is an index in which the target value (also referred to as "set value") to be satisfied in the lesion analysis model to be used is set by a user. In some embodiments, indices (e.g., the sensitivity and the false positive rate) having a trade-off relation are selected as a combination of the first index and the second index.

For example, the index correspondence information D2 is table information, prepared for each lesion analysis model, indicating a combination of a value of the first index and a value of the second index for each of various threshold values for lesion determination. For example, if a combination of the first index and the second index is set to the sensitivity (true positive rate) and the false positive rate, the table information described above corresponds to a ROC (Recever Operating Characteristic) curve. If a combination of the first index and the second index is set to the sensitivity and the precision, the table information described above corresponds to a PR (Precision Recall) curve. The above-described table information is not limited to information corresponding to a ROC curve or a PR curve, and may be information corresponding to a LROC (ROC-type curve for task of detection and localization) curve or a FROC (Free-response receiver operating characteristic) curve. It is noted that each record of the above-mentioned table information is associated with a threshold value for lesion determination corresponding to the combination of the value of the first index and the value of the second index included in the each record.

The table information described above is generated using test data having a plurality of records each of which is a combination of an endoscopic image for input and correct answer data indicating the presence or absence of a lesion region in the endoscopic image for input. In this case, the table information described above is generated by determining the correctness (specifically, the true positive, the false positive, the false negative, and the true negative) for each record of the above-described test data while changing the threshold value for lesion determination for each lesion analysis model, and aggregating the determination results with respect to each lesion analysis model and each threshold value for lesion determination. The table information described above is stored in advance in the memory 12 as the index correspondence information D2. Therefore, the index correspondence information D2 is the table information which shows the relation between the first index and the second index according to the actual results based on the test data.

(1-3) Outline of Lesion Analysis Process

A description will be given of the lesion analysis process, which is a processing related to the lesion analysis. In summary, on the basis of the index correspondence information D2, the image processing device 1 acquires a value (also referred to as "predicted value") of the second index, for each lesion analysis model, which is predicted on the assumption that the set value of the first index set by the user is satisfied, and then conducts the lesion analysis using the lesion analysis model corresponding to the best predicted value of the second index. Thus, the image processing device 1 can conduct the lesion analysis using such a lesion analysis model that is predicted to output the best result (i.e., best performance) for the second index while satisfying the set value of the first index set by the user.

Figure 3:
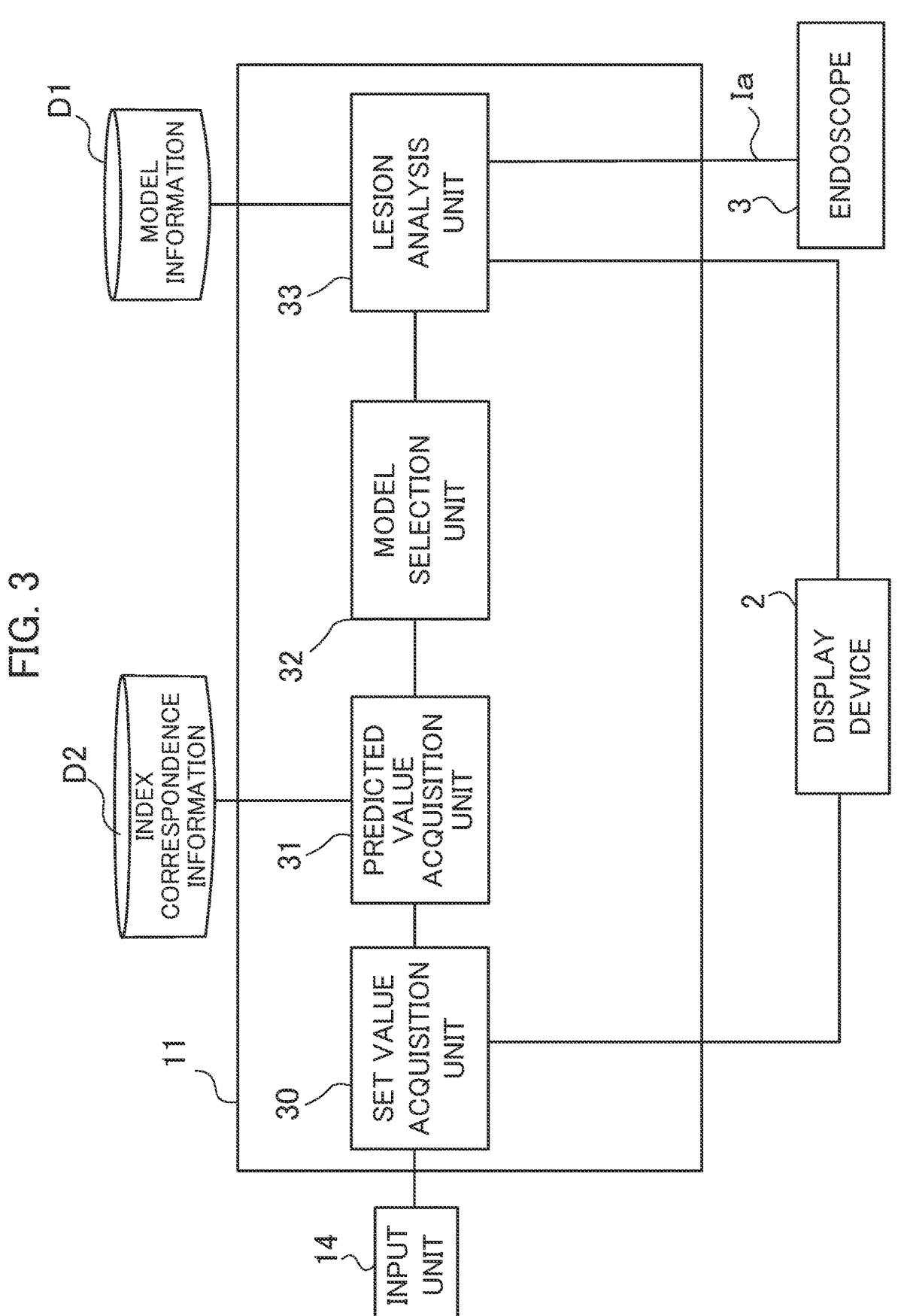
FIG. 3 It is a functional block diagram of the image processing device relating to the lesion analysis process in the first example embodiment.

FIG. 3 is a functional block diagram of the image processing device 1 relating to the lesion analysis process. The processor 11 of the image processing device 1 functionally includes a setting value acquisition unit 30, a predicted value acquisition unit 31, a model selection unit 32, and a lesion analysis unit 33. In FIG. 3, blocks to exchange data with each other are connected by a solid line, but the combination of blocks to exchange data with each other is not limited thereto. The same applies to the drawings of other functional blocks described below.

The set value acquisition unit 30 receives the input of the set value of the first index, and determines the set value of the first index based on the input signal received from the input unit 14 via the interface 13. In this case, in some embodiments, the set value acquisition unit 30 generates a display signal for displaying a display screen for receiving the input of the set value of the first index and supplies the display signal to the display device 2 to thereby display the above-described display screen on the display device 2. In this case, the setting value acquisition unit 30 may display a user interface for receiving an input specifying a numerical value of the first index, or may display a user interface for receiving an input specifying the level of the first index. In the latter example in which the sensitivity is used as the first index, the setting value acquisition unit 30 presents three options, "high sensitivity mode" corresponding to the sensitivity "0.95", "high specificity mode" corresponding to the sensitivity "0.80", and "intermediate mode" corresponding to the sensitivity "0.90", and receives an input for specifying an option to be employed, for example. The set value acquisition unit 30 notifies the predicted value acquisition unit 31 of the obtained set value of the first index.

For each lesion analysis model, the predicted value acquisition unit 31 acquires the predicted value of the second index that is predicted on the assumption that the set value of the first index supplied from the set value acquisition unit 30 is satisfied, on the basis of the index correspondence information D2. In this instance, the predicted value acquisition unit 31 extracts a record corresponding to the set value of the first index in the index correspondence information D2 for each lesion analysis model, and acquires the value of the second index recorded in the record as the predicted value of the second index for each lesion analysis model. In this case, if the value of the first index corresponding to the set value of the first index is not recorded in the index correspondence information D2, the predicted value acquisition unit 31 may acquire, as the above-mentioned predicted value, the value of the second index corresponding to the value of the first index closest to the set value, or may calculate the value of the second index corresponding to the set value of the first index through any interpolation process.

Further, for each lesion analysis model, the predicted value acquisition unit 31 acquires the threshold value for lesion determination associated with the combination of the set value of the first index and the predicted value of the second index in the index correspondence information D2. This threshold value for lesion determination is a threshold value for lesion determination to be used for the inference result outputted by each lesion determination model. Then, the predicted value acquisition unit 31 supplies the predicted value and the threshold value for lesion determination for each lesion analysis model, to the model selection unit 32.

The model selection unit 32 compares the predicted values of the second index for respective lesion analysis models supplied from the predicted value acquisition unit 31, and selects the lesion analysis model corresponding to the predicted value of the second index indicating the best accuracy among the predicted values as the lesion analysis model to be used for the lesion analysis. Then, the model selection unit 32 supplies the information indicating the selection result of the lesion analysis model, and the threshold value for lesion determination threshold corresponding to the selected lesion analysis model, to the lesion analysis unit 33. The model selection unit 32 reads the model information D1 corresponding to the selected lesion analysis model from the memory 12, and supplies the model information D1 to the lesion analysis unit 33.

The lesion analysis unit 33 conducts the lesion analysis based on: an endoscopic image Ia supplied from the endoscopic scope 3 after the start of the endoscopic examination; the lesion analysis model; and the threshold value for lesion determination supplied from the model selection unit 32. Thereby, the lesion analysis unit 33 determines whether or not there is a lesion area in the endoscopic image Ia. In this instance, the lesion analysis unit 33 builds the lesion analysis model by referring to the model information D1 corresponding to the lesion analysis model selected by the model selection unit 32. Then, based on the threshold value for lesion determination and an inference result outputted by the built lesion analysis model in response to the input of an endoscopic image Ia to the built lesion analysis model, the lesion analysis unit 33 determines whether or not there is a lesion region in the inputted endoscopic image Ia. For example, upon determining that the confidence score of the presence of the lesion region included in the inference result outputted from selected lesion analysis model is equal to or larger than the threshold value for lesion determination, the lesion analysis unit 33 determines that there is a lesion region. In contrast, upon determining that the confidence score is less than the threshold value for lesion determination, the lesion analysis unit 33 determines that there is no lesion region.

Further, the lesion analysis unit 33 may function as an output control means for outputting information by the display device or the audio output device. For example, the lesion analysis unit 33 displays the most-recently acquired endoscopic image Ia and the result of the lesion analysis on the display device 2. In this instance, the lesion analysis unit 33 generates display information Ib on the basis of the most-recently acquired endoscopic image Ia supplied from the endoscope 3 and the result of the lesion analysis based on the most-recently acquired endoscopic image Ia and supplies the generated display information Ib to the display device 2. In addition to the determination result of the existence of the lesion region, the result of the lesion analysis may further include information indicating the existence range of the lesion region outputted by the selected lesion analysis model. In this case, in addition to the determination result as to whether or not there is a lesion region in the most-recently acquired endoscopic image Ia, the lesion analysis unit 33 displays a mask image indicating the existence range of the lesion region in the most-recently acquired endoscopic image Ia or a bounding box surrounding the lesion region on the most-recently acquired endoscopic image Ia or the like on the display device 2. In some embodiments, upon determining that there is a lesion region, the lesion analysis unit 33 may control the sound output unit 16 to output a warning sound or voice guidance or the like notifying the user that there is a lesion region.

Further, for example, the lesion analysis unit 33 may determine and output a coping method (remedy) based on a result of the lesion analysis of the subject and a model generated through machine learning of a correspondence relation between a result of the lesion analysis and the corresponding coping method. The determination approach for the coping method is not limited to the approach described above. Outputting such a coping method can further assist the examiner's decision making.

Each component of the setting value acquisition unit 30, the predicted value acquisition unit 31, the model selection unit 32, and the lesion analysis unit 33 can be realized, for example, by the processor 11 which executes a program. In addition, the necessary program may be recorded in any non-volatile storage medium and installed as necessary to realize the respective components. In addition, at least a part of these components is not limited to being realized by a software program and may be realized by any combination of hardware, firmware, and software. At least some of these components may also be implemented using user-programmable integrated circuitry, such as FPGA (Field-Programmable Gate Array) and microcontrollers. In this case, the integrated circuit may be used to realize a program for configuring each of the above-described components. Further, at least a part of the components may be configured by a ASSP (Application Specific Standard Produce), ASIC (Application Specific Integrated Circuit) and/or a quantum processor (quantum computer control chip). In this way, each component may be implemented by a variety of hardware. The above is true for other example embodiments to be described later. Further, each of these components may be realized by the collaboration of a plurality of computers, for example, using cloud computing technology.

(1-4) Specific Examples of Model Selection

Next, a description will be given of specific examples of the selection of the lesion analysis model by the model selection unit 32.

Figure 4:
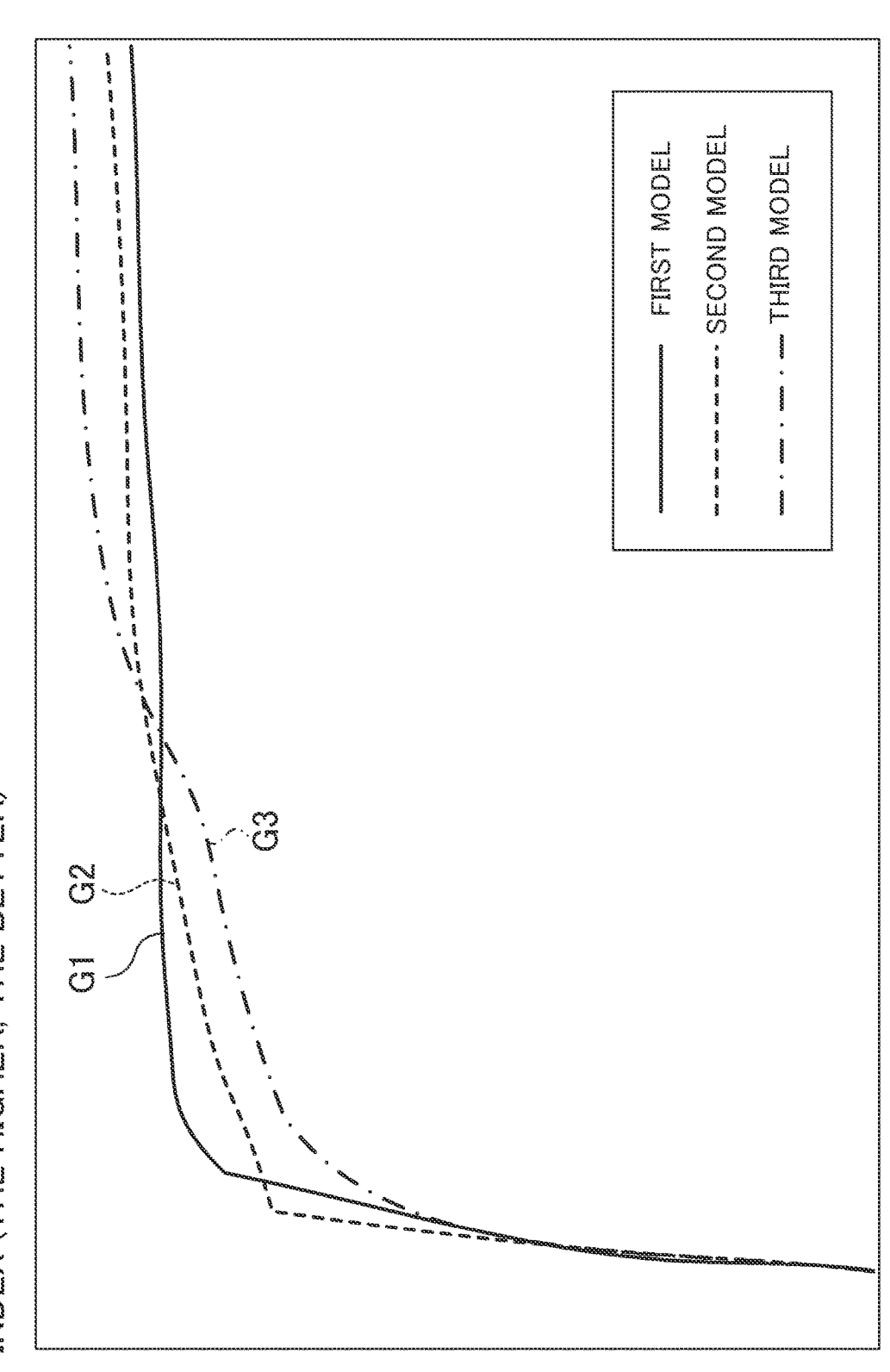
FIG. 4 It illustrates a graph showing the correspondence relation between the first index and the second index indicated by index correspondence information.

FIG. 4 is a graph showing the correspondence between the first index and the second index indicated by the index correspondence information D2. Here, three models (the first model, the second model, and the third model) are registered in the model information D1 as lesion analysis models, and the graph G1 corresponding to the first model, the graph G2 corresponding to the second model, and the graph G3 corresponding to the third model are respectively shown. The graphs G1 to G3 each is a curve on two-dimensional coordinates with the first index and the second index as coordinate axes and is obtained by aggregating the determination results regarding the correctness (in detail, true positive, false positive, false negative, and true negative) of the inference results based on the test data while changing the threshold value for lesion determination for each three model.

The first index is an index (e.g., sensitivity) indicating that the higher the value is, the greater the accuracy becomes, the second index is an index (e.g., false positive rate) indicating that the lower the value is, the greater the accuracy becomes. The combination of the first index and the second index shown in FIG. 4 is an example. For example, the first index may be an index (e.g., false positive rate) indicating that the lower the value is, the greater the accuracy becomes while the second index is an index (e.g., sensitivity) indicating that the higher the value is, the greater the accuracy becomes. Here, the first index is a trade-off relation with the second index, and that is a relation that, when one index becomes better, the other index deteriorates. When the sensitivity is used as the first index and the false positive rate is used as the second index, the graphs G1 to G3 correspond to ROC curves. Any two graphs selected from the graphs G1 to G3 have at least one intersecting point at which the two graphs intersect each other.

Figure 5:
FIG. 5 It is a diagram showing predicted values of the second index of the respective models when a set value Vs1 of the first index is set.

FIG. 5 shows the graphs G1 to G3 with clear indication of the predicted values "Vp11" to "Vp13" of the second index for each model in the case of the set value "Vs1" of the first index. When the set value Vs1 of the first index is set by the user, the predicted value acquisition unit 31 acquires the predicted value of the second index on the assumption that the set value Vs1 of the first index is satisfied for the first model, the second model, and the third model. For example, in the case of the first model, the predicted value acquisition unit 31 recognizes the corresponding point "P11" corresponding to the set value Vs1 of the first index in the graph G1, and then acquires the value (Vp11 in this case) of the second index corresponding to the corresponding point P11 as the predicted value of the second index. Similarly, in the case of the second model and third model, the predicted value acquisition unit 31 recognizes the corresponding points "P12" and "P13" corresponding to the set value Vs1 of the first index and then acquires the values (Vp12 and Vp13 in this case) of the second index corresponding to the corresponding points P12 and P13 as predicted values of the second index, respectively.

Then, the model selection unit 32 identifies the predicted value indicating the best accuracy among the predicted values of the second index of the respective models, and selects a lesion analysis model corresponding to the identified predicted value of the second index. Since the predicted value Vp12 among the predicted values Vp11 to Vp13 of the second index is the lowest value and thus most excellent, the model selection unit 32 selects the second model corresponding to the predicted value Vp12. Then, the lesion analysis unit 33 conducts the lesion analysis based on the endoscopic image Ia using the second model selected in this way and the threshold value for lesion determination associated with the corresponding point P12. Thus, the image processing device 1 can conduct the lesion analysis using the lesion analysis model predicted to output the best result (i.e., the best performance) regarding the second index while satisfying the set point Vs1 of the first index.

Figure 6:
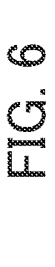
FIG. 6 It is a diagram showing predicted values of the second index of the respective models when a set value Vs2 of the first index is set.

FIG. 6 shows the graphs G1 to G3 with clear indication of the predicted values "Vp21" to "Vp23" of the second index for each model in the case of the set value "Vs2" of the first index. When the set value Vs2 of the first index is set by the user, the predicted value acquisition unit 31 acquires the predicted value of the second index on the assumption that the set value Vs2 of the first index is satisfied for the first model, the second model, and the third model. For example, in the case of the first model, the predicted value acquisition unit 31 recognizes the corresponding point "P21" corresponding to the set value Vs2 of the first index in the graph G1, and then acquires the value (Vp21 in this case) of the second index corresponding to the corresponding point P21 as the predicted value of the second index. Similarly, in the case of the second model and the third model, the predicted value acquisition unit 31 recognizes the corresponding points "P22" and "P23" corresponding to the set value Vs2 of the first index, and then acquires the values (Vp22 and Vp23 in this case) of the second index corresponding to the corresponding points P22 and P23 as the predicted values of the second index, respectively.

Then, the model selection unit 32 identifies the predicted value indicating the best accuracy among the predicted values of the second index regarding respective models, and selects the lesion analysis model corresponding to the identified predicted value of the second index. Since the predicted value Vp21 among the predicted values Vp21 to Vp23 of the second index is the lowest value and thus most excellent, the model selection unit 32 selects the first model corresponding thereto. Since the graphs G1 to G3 have intersecting points, the model having the best predicted value of the second index changes from the second model to the first model due to the change in the set value of the first index from the value Vs1 to the value Vs2. Then, the lesion analysis unit 33 conducts the lesion analysis based on the endoscopic image Ia using the first model selected in this way and the threshold value for lesion determination associated with the corresponding point P21. Thus, the image processing device 1 can conduct the lesion analysis using the lesion analysis model predicted to output the best result (i.e., the best performance) regarding the second index while satisfying the set point Vs2 of the first index.

(1-5) Processing Flow

Figure 7:
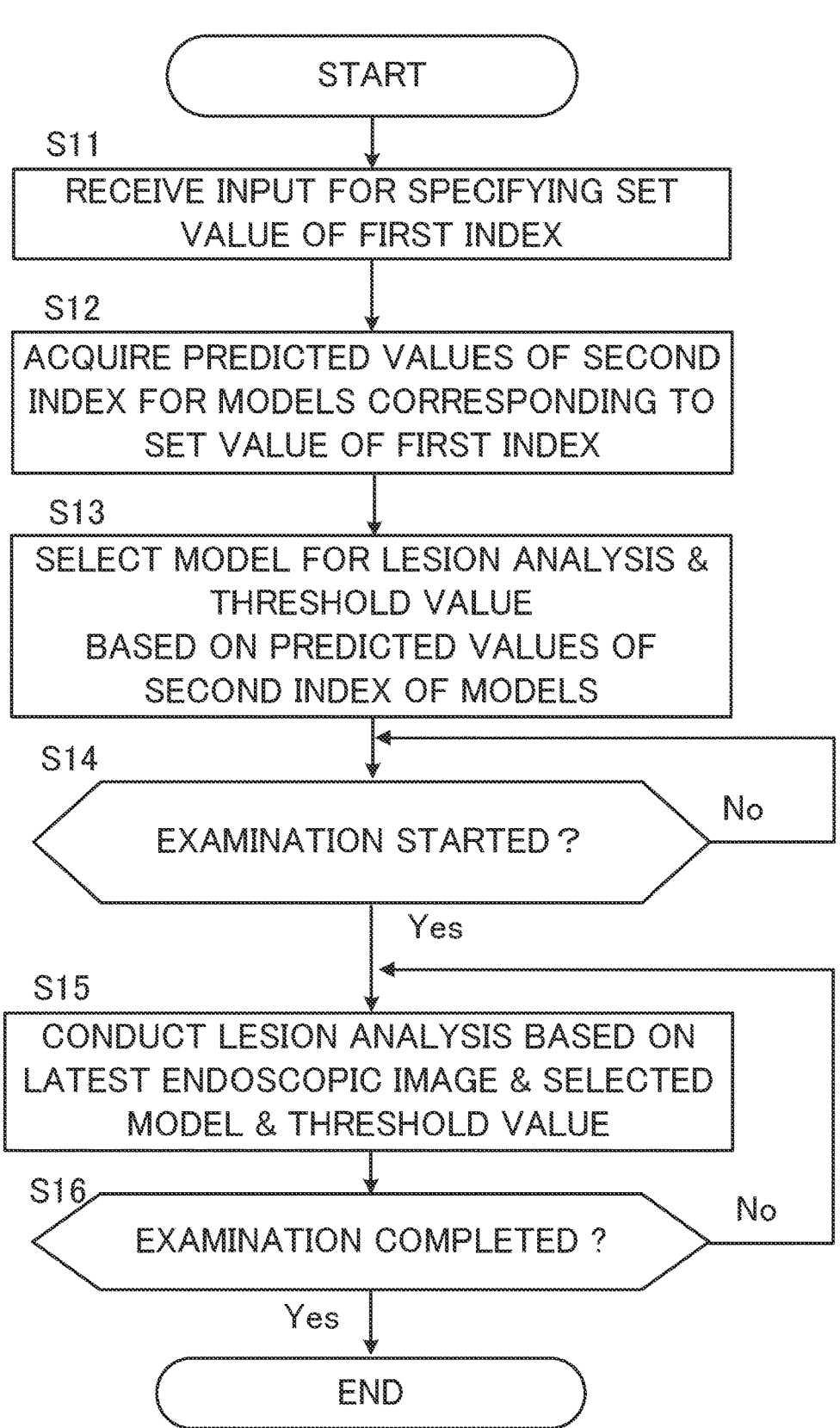
FIG. 7 It is an example of a flowchart showing an outline of the process performed by the image processing device in the first example embodiment.

FIG. 7 is an example of a flowchart illustrating an outline of the process that is executed by the image processing device 1 according to the first example embodiment. The image processing device 1 starts the process of the flowchart before the start of the endoscopic examination.

First, the image processing device 1 receives an input for specifying the setting value of the first index (step S11). For example, the image processing device 1 receives an input signal specifying the set value of the first index from the input unit 14. Then, the image processing device 1 acquires the predicted value of the second index for each lesion analysis models corresponding to the set value of the first index specified at step S11 (step S12). In this instance, for each lesion analysis model, the image processing device 1 refers to the index correspondence information D2 and acquires the value of the second index associated in the index correspondence information D2 with the set value of the first index as the predicted value described above.

Next, the image processing device 1 selects the lesion analysis model for the lesion analysis and the threshold value for lesion determination, based on the predicted values of the second index of the respective lesion analysis models (step S13). In this instance, the image processing device 1 identifies a lesion analysis model corresponding to the best predicted value of the second index, and the threshold value for lesion determination associated with the best predicted value in the index correspondence information D2.

Then, the image processing device 1 determines whether or not the endoscopic examination has started (step S14). For example, upon determining that the image processing device 1 receives an endoscopic image Ia from the endoscope 3 through the interface 13, the image processing device 1 determines that the endoscopic examination has started. If the endoscopic examination has not started (step S14; No), the image processing device 1 performs the process at step S14 continuously.

Upon determining that the endoscopic examination has started (step S14; Yes), the image processing device 1 conducts the lesion analysis on the basis of the most-recently acquired endoscopic image Ia received from the endoscope 3 through the interface 13 and the lesion analysis model and the threshold value for lesion determination selected at step S13 (step S15). In addition, the image processing device 1 displays the most-recently acquired endoscopic image Ia and the result of the lesion analysis on the display device 2.

Then, after the process at step S15, the image processing device 1 determines whether or not the endoscopic examination has been completed (step S16). For example, the image processing device 1 determines that the endoscopic examination has been completed if a predetermined input or the like to the input unit 14 or the operation unit 36 is detected. Upon determining that the endoscopic examination has been completed (step S16; Yes), the image processing device 1 ends the process of the flowchart. On the other hand, upon determining that the endoscopic examination has not been completed (step S16; No), the image processing device 1 returns gets back to the process at step S15. Then, the image processing device 1 proceeds with the process at step S15 for an endoscopic image Ia newly generated by the endoscope 3.

(1-6) Modifications

Next, a description will be given of preferred modifications to the first example embodiment described above. The following modifications may be applied to the first example embodiment described above in any combination.

Modification 1-1

Instead of acquiring the set value of the first index based on the input signal from the input unit 14, the set value acquisition unit 30 may acquire the set value of the first index from the memory 12 or an external device.

In this case, for example, when the endoscopic examination is started, the image processing device 1 reads or receives the set value of the first index from the memory 12 or an external device in which the set value of the first index is stored. Thereafter, the image processing device 1 selects the lesion analysis model on the basis of the acquired set value of the first index and executes the lesion analysis on the basis of the selected lesion analysis model and the endoscopic image Ia acquired in the endoscopic examination. According to this aspect, the image processing device 1 acquires the set value of the first index, thereby conducting the lesion analysis based on the lesion analysis model predicted to output a best performance which satisfies the set value of the first index.

Modification 1-2

The model information D1 and the index correspondence information D2 may be stored in a storage device separate from the image processing device 1.

Figure 8:
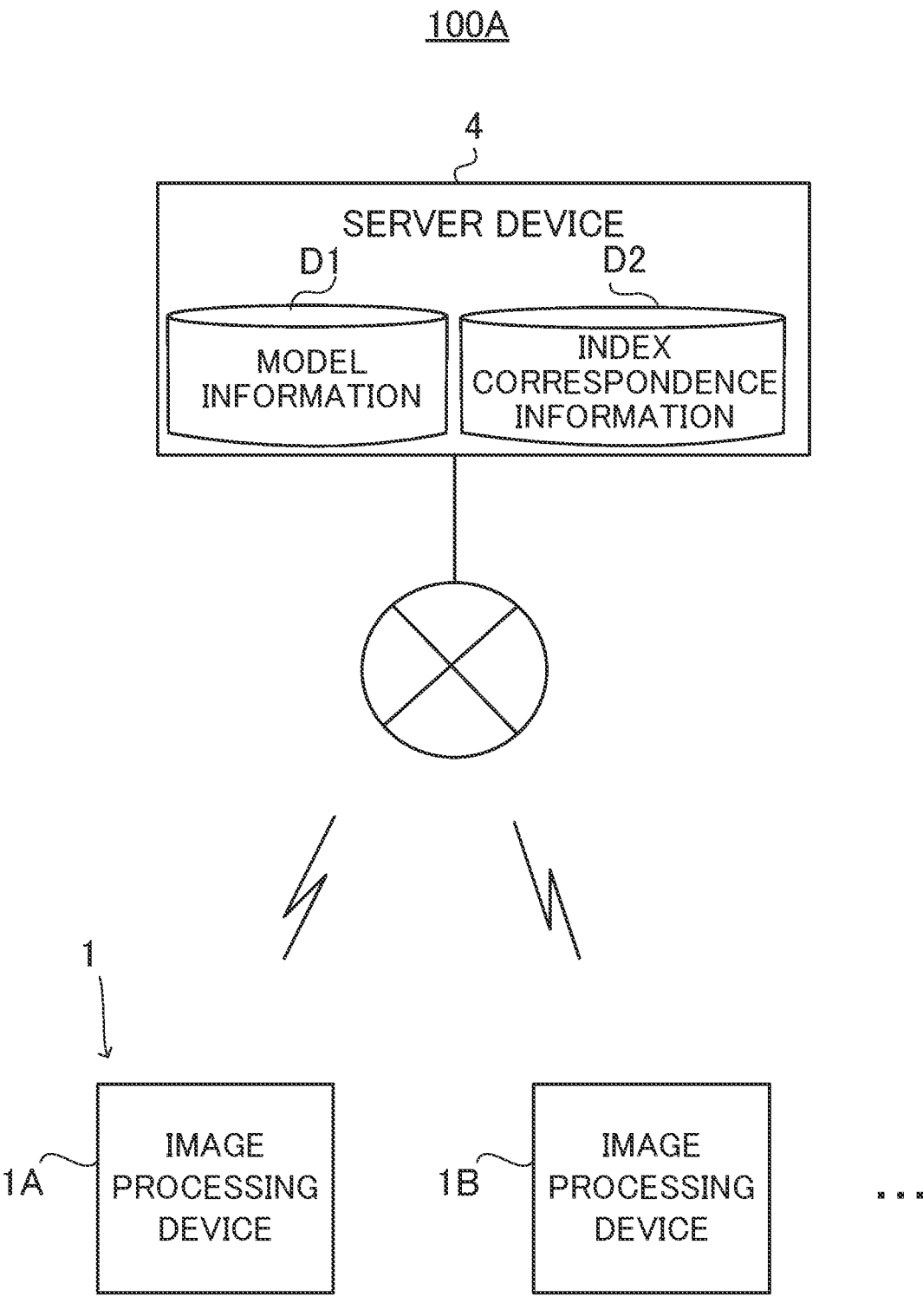
FIG. 8 It is a schematic diagram of the endoscopic examination system according to a modification of the first example embodiment.

FIG. 8 is a schematic configuration diagram of an endoscopic examination system 100A according to the modification. For simplicity, the display device 2 and the endoscope 3 and the like are not shown. The endoscopic examination system 100A includes a server device 4 that stores the model information D1 and the index correspondence information D2. Further, the endoscopic examination system 100A includes a plurality of image processing devices 1 (1A, 1B, . . . ) capable of data communication with the server-device 4 via a network.

In this instance, the respective image processing devices 1 refer to the model information D1 and the index correspondence information D2 via the network. In this case, the interface 13 of each image processing device 1 includes a communication interface such as a network adapter for data communication. In this configuration, the image processing device 1, as in the above-described example embodiment, refers to the model information D1 and the index correspondence information D2, suitably executing the process related to the lesion detection.

Second Example Embodiment

In the second example embodiment, instead of using the predicted values of the second index to select the lesion analysis model, the image processing device 1 uses the predicted values of the second index to set the weight for the inference results of respective lesion analysis models in the case where the presence or absence of a lesion is determined based on integrated inference results of a plurality of lesion analysis models. Hardware configuration of the image processing device 1 in the second example embodiment is assumed to be identical to the configuration shown in FIG. 2. Hereinafter, the same components as those in the first example embodiment are denoted by the same reference numerals, and a description thereof will be omitted as appropriate.

(2-1) Functional Blocks

Figure 9:
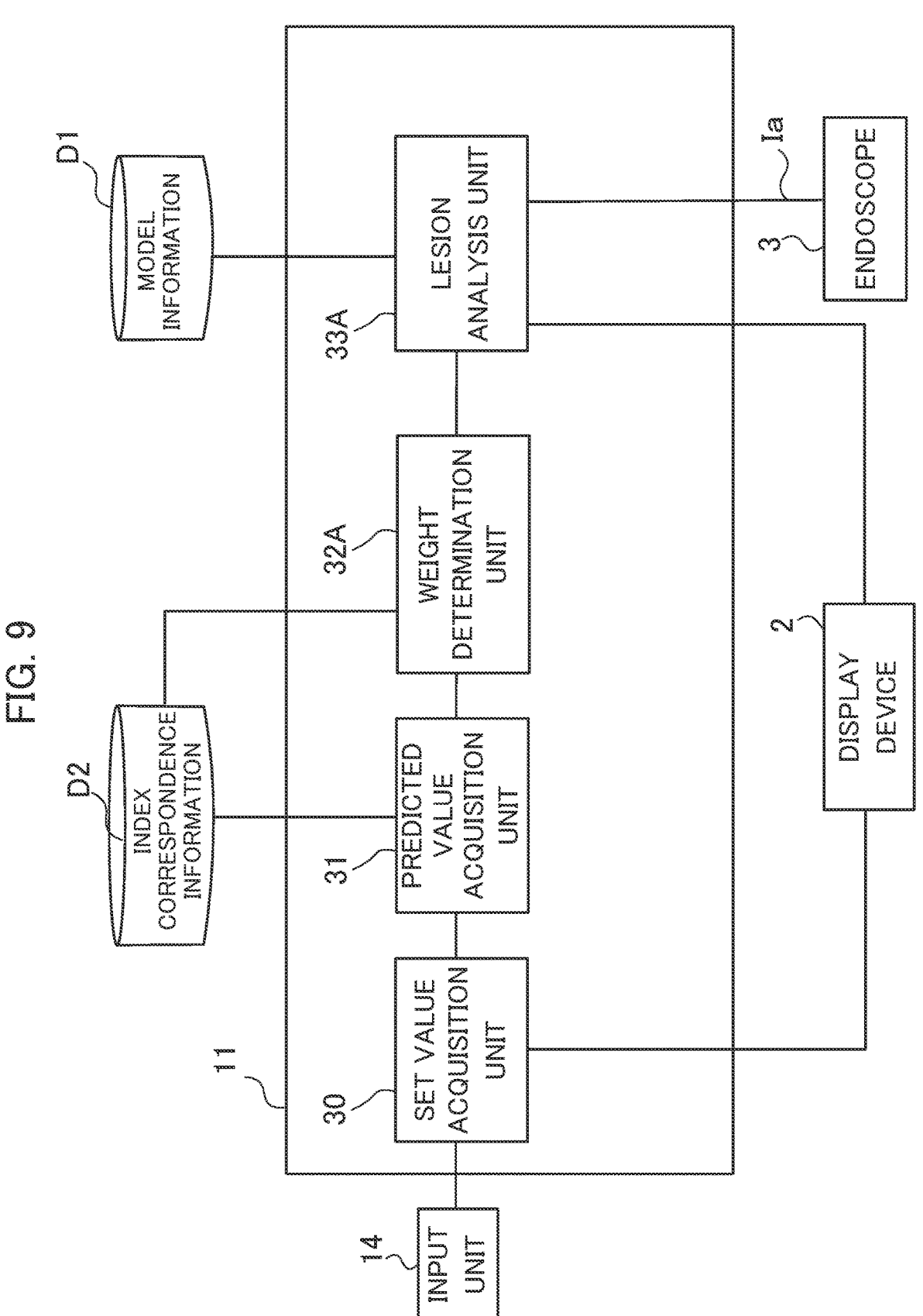
FIG. 9 It is a functional block diagram of the image processing device relating to the lesion analysis process in a second example embodiment.

FIG. 9 is a functional block diagram of the image processing device 1 according to the second example embodiment. The processor 11 of the image processing device 1 functionally includes a setting value acquisition unit 30, a predicted value acquisition unit 31, a weight determination unit 32A, and a lesion analysis unit 33A. The processes performed by the setting value acquisition unit 30 and the predicted value acquisition unit 31 are the same as the processes in the first example embodiment, and thus description thereof will be omitted.

Based on the predicted values of the second index corresponding to the respective lesion analysis models which are supplied from the predicted value acquisition unit 31, the weight determination unit 32A determines weights to be used for integrating the inference results of the respective lesion analysis models, wherein the parameters of the respective lesion analysis models are registered in the model information D1. For example, the weight determination unit 32A sets the respective weights when calculating an ensemble average of the confidence scores of the presence of a lesion region based on the predicted values of the second index. In this case, for example, provided that the lower the value of the second index is, the greater the accuracy becomes, the weight determination unit 32A sets, as the weight, a value (e.g., the inverse of the predicted value or the value obtained by subtracting the predicted value from the maximum value of the second index) having a negative correlation with the corresponding predicted value of the second index. On the other hand, provided that the higher the value of the second index, the greater the accuracy becomes, the weight determination unit 32A sets, as the weight, a value (e.g., the predicted value of the second index as it is) having a positive correlation with the predicted value of the second index. If an equation or a table which indicates the correspondence between the predicted value of the second index and the weight is stored in the memory 12, the weight determination unit 32A may determine the weight from the predicted value of the second index by referring to the equation or the table. In some embodiments, the weight determination unit 32A may normalize the above-described weights such that the total value of the weights (the sum of the weights) used for integrating the inference results of the respective lesion analysis models is equal to 1. The weight determination unit 32A supplies the lesion analysis unit 33A with information indicating the weight for each lesion analysis model.

The lesion analysis unit 33A inputs an endoscopic image Ia into each of the lesion analysis models whose parameters are registered in the model informational D1, and acquires the inference results outputted by the respective lesion analysis models. Then, lesion analysis unit 33A integrates the inference results outputted by the respective lesion analysis models using the weights determined by the weight determination unit 32A, and determines the presence or absence of the lesion region of the inputted endoscopic image Ia on the basis of the integrated inference result.

The specific example of the integration of the inference results based on the weights will be described. A description herein will be given of the example shown in FIG. 5 in which the predicted value acquisition unit 31 acquires the predicted values Vp11 to Vp13 of the second index for the set value Vs1 of the first index. It is assumed that the confidence score which the first model outputs is "s1", the confidence score which the second model outputs is "s2", and the confidence score which the third model outputs is "s3".

In this instance, for example, the lesion analysis unit 33A obtains the final confidence score "s" to be compared with the threshold value for lesion determination by weighted averaging as follows. Here, as an example, each of the predicted values Vp11 to Vp13 of the second index is assumed to have a value range from the minimum value 0 to the maximum value 1.

$$s = \{(s1 \times (1 - Vp11)) + (s2 \times (1 - Vp12)) + (s3 \times (1 - Vp13))\}$$
$$/(Vp11 + Vp12 + Vp13)$$

In the above equation, as an example, the lesion analysis unit 33A sets, as the weight, a value obtained by subtracting the predicted value from the largest value of the second index. Instead of this example, the lesion analysis unit 33A may set, as the weight, any value having a negative correlation with the predicted value of the second index, such as the inverse of the predicted value of the second index.

The lesion analysis 33A then determines that there is a lesion region if the final confidence score s is equal to or larger than the threshold value for lesion determination, whereas the lesion analysis 33A determines that there is no lesion region if the final confidence score s is smaller than the threshold value for lesion determination. It is noted that the threshold value for lesion determination used here may be a predetermined value stored in advance in the memory 12 or may be the average value (also includes a weighted average value based on the predicted values of the second index) of the threshold values for lesion determination corresponding to the predicted values of the second index for respective lesion analysis models.

As described above, the image processing device 1 integrates the inference results of a plurality of lesion analysis models whose parameters are recorded in the model information D1 by weighting based on the predicted values of the second index, thereby performing more highly accurate lesion analysis.

(2-2) Processing Flow

Figure 10:
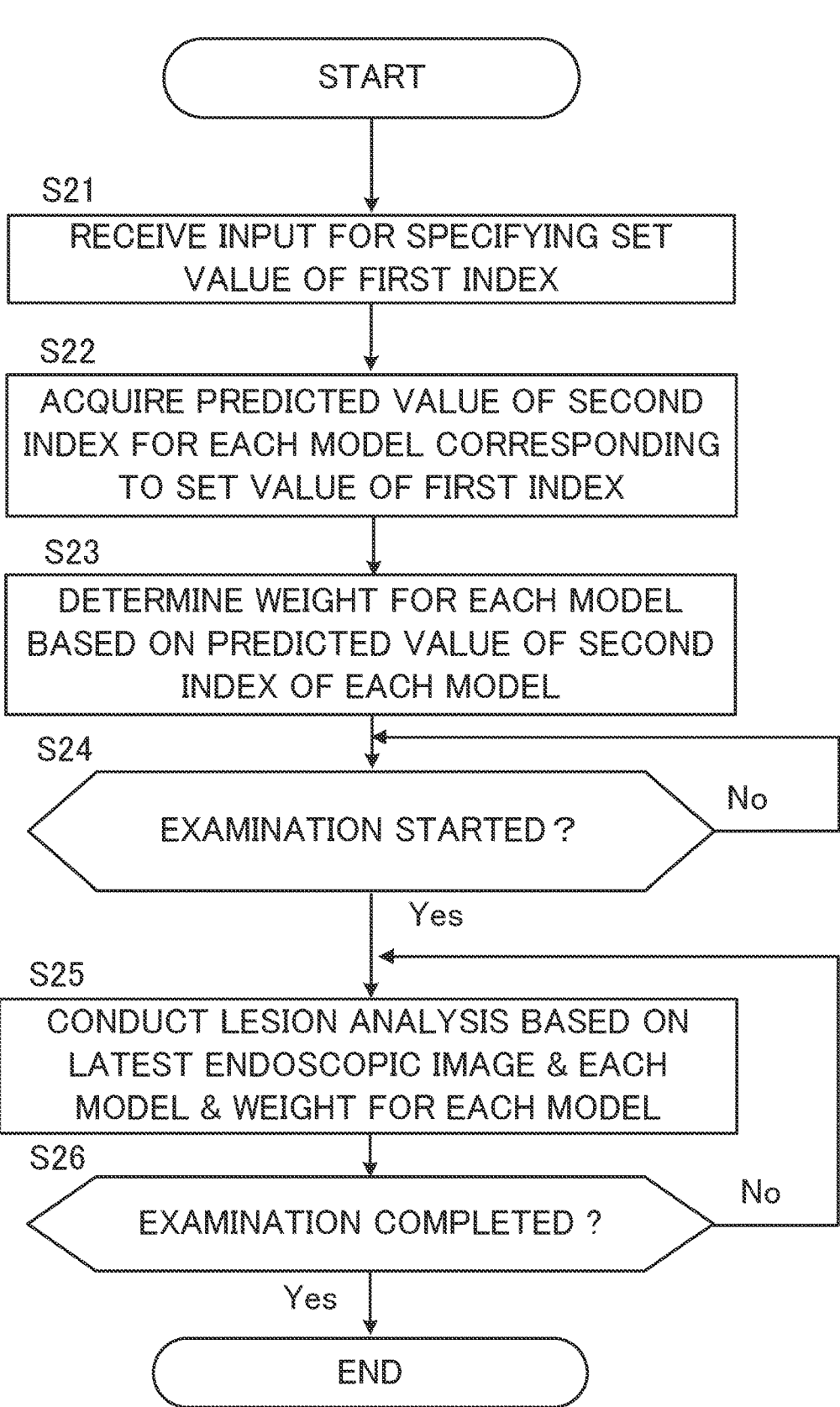
FIG. 10 It is an example of a flowchart showing an outline of the process performed by the image processing device in the second example embodiment.

FIG. 10 is an example of a flowchart illustrating an outline of the process that is executed by the image processing device 1 in the second example embodiment. The image processing device 1 starts the process of the flowchart before the start of the endoscopic examination.

First, the image processing device 1 receives an input for specifying the set value of the first index (step S21). Then, the image processing device 1 acquires the predicted value of the second index of each lesion analysis model corresponding to the set value of the first indices specified at step S11 (step S22).

Next, the image processing device 1 determines the weight for each lesion analysis model on the basis of the predicted value of the second index of each lesion analysis model whose parameters are registered in the model information D1 (step S23). Then, the image processing device 1 determines whether or not the endoscopic examination has started (step S24). If the endoscopic examination has not started (step S24; No), the image processing device 1 performs the process at step S24 continuously.

Upon determining that the endoscopic examination has started (step S24; Yes), the image processing device 1 executes the lesion analysis on the basis of the most-recently acquired endoscopic image Ia received from the endoscope 3 through the interface 13, each lesion analysis model, and the weight for each lesion analysis model (step S25). In addition, the image processing device 1 displays the most-recently acquired endoscopic image Ia and the result of the lesion analysis on the display device 2.

Then, the image processing device 1 determines whether or not the endoscopic examination has been completed after the process at step S15 (step S26). Upon determining that the endoscopic examination has been completed (step S26; Yes), the image processing device 1 ends the process of the flowchart. On the other hand, upon determining that the endoscopic examination has not been completed (step S26; No), the image processing device 1 gets back to the process at step S25. Then, the image processing device 1 performs the process at step S25 for an endoscopic image Ia newly generated by the endoscope 3.

(2-3) Modifications

Next, a description will be given of preferred modifications to the second example embodiment described above. The modifications described in the section "(1-6) Modifications" and the following modifications may be applied to the second example embodiment described above in any combination.

Modification 2-1

The image processing device 1 may be executed by switching between the lesion analysis (i.e., the lesion analysis using the selected single lesion analysis model) according to the first example embodiment and the lesion analysis (i.e., the lesion analysis using a plurality of lesion analysis models) according to the second example embodiment.

In the first example, the image processing device 1 performs a lesion analysis according to the first example embodiment at the start of the endoscopic examination, and then switches from the lesion analysis according to the first example embodiment to the lesion analysis according to the second example embodiment, upon detecting a disorder (also referred to as "background disorder") other than the target disorder in the most-recently acquired endoscopic image Ia. Examples of the background disorder include inflammation, bleeding, Barrett esophagus if the examination target is the esophagus, and any other disorder (condition) other than the target disorder. In this case, for example, the memory 12 stores information regarding a model configured to output information regarding a background disorder when an endoscopic image is inputted thereto. The image processing device 1 inputs a most-recently acquired endoscopic image Ia to the model and then determines whether or not there is a background disorder based on the information outputted by the model in response to the input of the most-recently acquired endoscopic image Ia. For example, the above-described model is a classification model configured to output a classification result indicative of the presence or absence (and the scores thereof) of a background lesion when an endoscopic image is inputted thereto. The classification result outputted by the above-described model may indicate the presence (and the score thereof) of a specific type of a background disorder, or may indicate the type (and the score thereof) of the existing background lesion. The model described above may be any machine learning model (including any statistical model, hereinafter the same) such as a neural network and a support vector machine.

As such, in the first example, upon detecting a background disorder, the image processing device 1 performs a lesion analysis according to the second example embodiment in which it is expected that a more accurate inference result can be obtained. If the background disorder has not been detected, the image processing device 1 switches from the lesion analysis according to the second example embodiment to the lesion analysis according to the first example embodiment. In this way, it conducts the lesion analysis according to the second example embodiment which comes with high calculation load only in important scenes that the lesion analysis with high accuracy is required. Thereby, it is possible to acquire a result of the lesion analysis with high accuracy in important scenes that the lesion analysis with high accuracy is required, while suitably reducing the calculation load in other scenes.

In the second example, the image processing device 1 switches between a lesion analysis according to the first example embodiment and a lesion analysis according to the second example embodiment, based on an input (i.e., an external input) from the examiner through the input unit 14 or the operation unit 36. In this case, for example, the image processing device 1 conducts the lesion analysis according to the first example embodiment at the start of the endoscopic examination and then switches from the lesion analysis according to the first example embodiment to the lesion analysis according to the second example embodiment upon detecting a predetermined external input. Further, after switching to the lesion analysis according to the second example embodiment, upon detecting a predetermined external input, the image processing device 1 switches from the lesion analysis according to the second example embodiment to the lesion analysis according to the first example embodiment.

As such, in the second example, based on the input (i.e., the external input) from the examiner through the input unit 14 or the operation unit 36, it switches between the lesion analysis according to the first example embodiment and the lesion analysis according to the second example embodiment. Even according to this example, it conducts the lesion analysis according to the second example embodiment which comes with high calculation load only in important scenes that the lesion analysis with high accuracy is required. Thereby, it is possible to acquire a result of the lesion analysis with high accuracy in important scenes that the lesion analysis with high accuracy is required, while suitably reducing the calculation load in other scenes.

It is noted that, in this modification, the lesion analysis according to the first example embodiment is an example of the "first mode" and the lesion analysis according to the second example embodiment is an example of the "second mode". The presence or absence of detection of a background lesion in the first example, and the presence or absence of detection of an external input in the second example are examples of the "predetermined condition".

Modification 2-2

The image processing device 1 may conduct a lesion analysis in which the first example embodiment and the second example embodiment are combined.

For example, the image processing device 1 selects a predetermined number (two or more number) of lesion analysis models corresponding to top superior predicted values of the second index from respective lesion analysis models whose parameters are recorded in the model information D1. Then, the image processing device 1 integrates the inference results of the selected predetermined number of lesion analysis models by using the weights set on the basis of the corresponding predicted values of the second index. According to this aspect, the image processing device 1 uses the limited lesion analysis models predicted to have a good performance for the lesion analysis, and can finally acquire a highly accurate inference result by integrating the inference results of the limited lesion analysis models.

Third Example Embodiment

Figure 11:
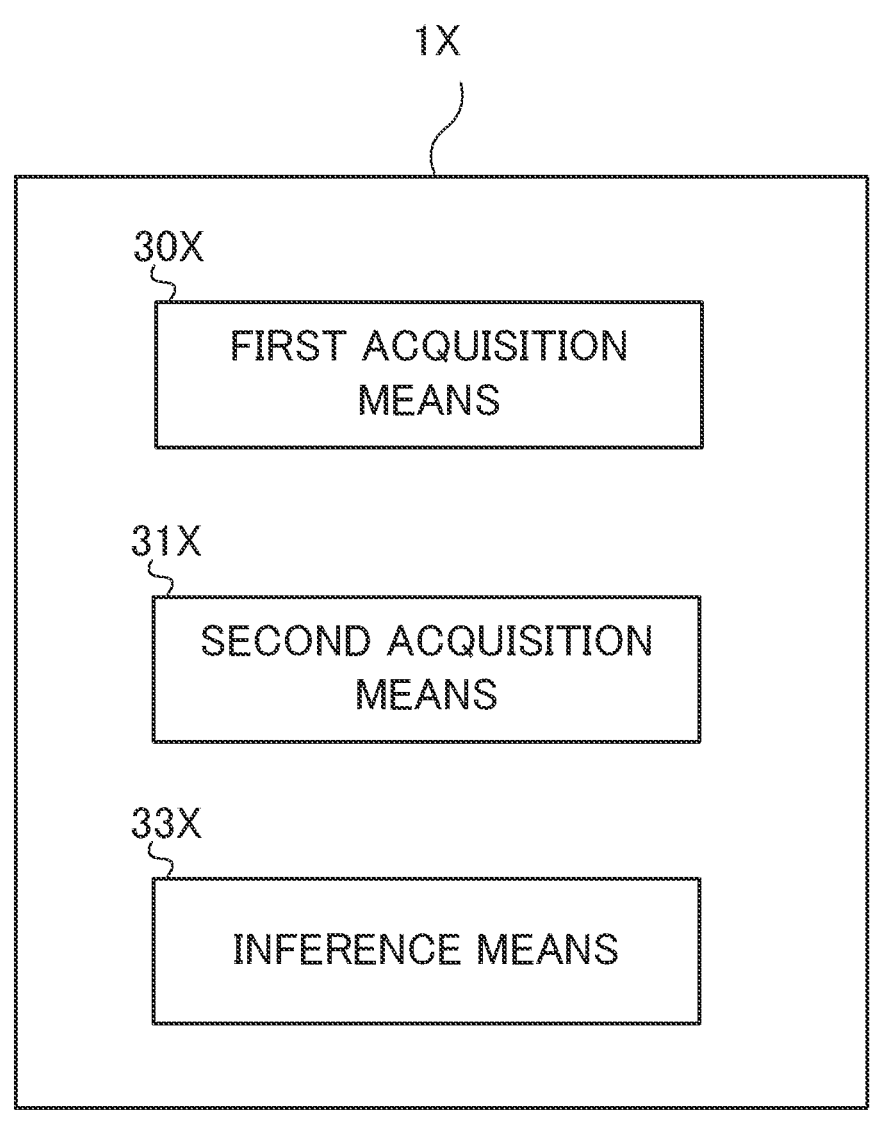
FIG. 11 It is a block diagram of the image processing device according to a third example embodiment.

FIG. 11 is a block diagram of an image processing device 1X according to a third example embodiment. The image processing device 1X includes a first acquisition means 30X, a second acquisition means 31X, and an inference means 33X. The image processing device 1X may be configured by a plurality of devices.

The first acquisition means 30X is configured to acquire a set value of a first index indicating an accuracy relating to a lesion analysis. Examples of the first acquisition means 30X include the set value acquisition unit 30 in the first example embodiment and the second example embodiment.

The second acquisition means 31X is configured to acquire, for each of plural models which make inference regarding a lesion, a predicted value of a second index, which is an index of the accuracy other than the first index, on an assumption that the set value of the first index is satisfied. Examples of the second acquisition means 31X include a predicted value acquisition unit 31 in the first example embodiment and the second example embodiment.

The inference means 33X is configured to make inference regarding the lesion included in an endoscopic image of an examination target, based on the predicted value of the second index and the plural models. Examples of the inference means 33X include the model selection unit 32 and the lesion analysis unit 33 in the first example embodiment, and the weight determination unit 32A and the lesion analysis unit 33A in the second example embodiment.

Figure 12:
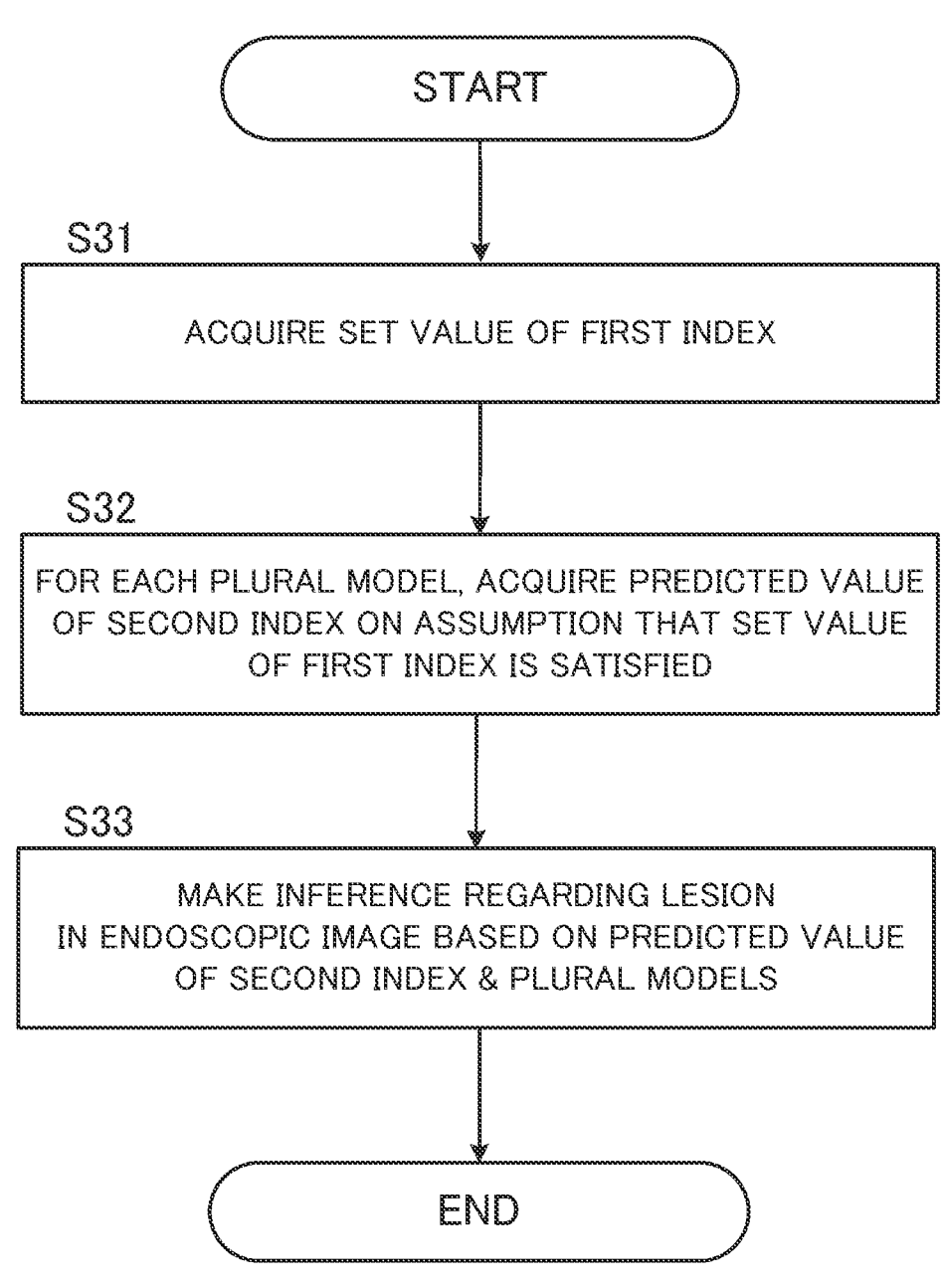
FIG. 12 It is an example of a flowchart executed by the image processing device in the third example embodiment.

FIG. 12 is an example of a flowchart showing a processing procedure in the third example embodiment. The first acquisition means 30X acquires a set value of a first index indicating an accuracy relating to a lesion analysis (step S31). The second acquisition means 31X acquires, for each of plural models which make inference regarding a lesion, a predicted value of a second index, which is an index of the accuracy other than the first index, on an assumption that the set value of the first index is satisfied (step S32). The inference means 33X makes inference regarding the lesion included in an endoscopic image of an examination target, based on the predicted value of the second index and the plural models (step S33).

According to the third example embodiment, taking into account the predicted values of the second index of the respective models on the assumption that the set values of the first indices are satisfied, the image processing device 1X can suitably makes inference regarding a lesion in the endoscopic image in which the examination target is photographed.

In the example embodiments described above, the program is stored by any type of a non-transitory computer-readable medium (non-transitory computer readable medium) and can be supplied to a control unit or the like that is a computer. The non-transitory computer-readable medium include any type of a tangible storage medium. Examples of the non-transitory computer readable medium include a magnetic storage medium (e.g., a flexible disk, a magnetic tape, a hard disk drive), a magnetic-optical storage medium (e.g., a magnetic optical disk), CD-ROM (Read Only Memory), CD-R, CD-R/W, a solid-state memory (e.g., a mask ROM, a PROM (Programmable ROM), an EPROM (Erasable PROM), a flash ROM, a RAM (Random Access Memory)). The program may also be provided to the computer by any type of a transitory computer readable medium. Examples of the transitory computer readable medium include an electrical signal, an optical signal, and an electromagnetic wave. The transitory computer readable medium can provide the program to the computer through a wired channel such as wires and optical fibers or a wireless channel.

The whole or a part of the example embodiments described above (including modifications, the same applies hereinafter) can be described as, but not limited to, the following Supplementary Notes.

[Supplementary Note 1]

An image processing device comprising:

a first acquisition means configured to acquire a set value of a first index indicating an accuracy relating to a lesion analysis;

a second acquisition means configured to acquire, for each of plural models which make inference regarding a lesion, a predicted value of a second index, which is an index of the accuracy other than the first index, on an assumption that the set value of the first index is satisfied; and an inference means configured to make inference regarding the lesion included in an endoscopic image of an examination target, based on the predicted value of the second index and the plural models.

[Supplementary Note 2]

The image processing device according to Supplementary Note 1, wherein, for each of plural models, the second acquisition means is configured to acquire correspondence information indicative of a correspondence relation between the first index and the second index and acquire, as the predicted value, a value of the second index corresponding to the set value according to the correspondence information.

[Supplementary Note 3]

The image processing device according to Supplementary Note 2, wherein the correspondence information indicates an ROC curve, an LROC curve, an FROC curve, or a PR curve.

[Supplementary Note 4]

The image processing device according to Supplementary Note 2, wherein curves of the plural models on two-dimensional coordinates with the first index and the second index as coordinate axes include intersecting points at which the curves intersect each other.

[Supplementary Note 5]

The image processing device according to Supplementary Note 1, wherein the inference means is configured to select a model with a best accuracy indicated by the predicted value from the plural models, and make the inference based on the selected model and the endoscopic image.

[Supplementary Note 6]

The image processing device according to Supplementary Note 1, wherein the inference means is configured to generate an inference result obtained by weighting, based on the predicted value, each inference result based on the endoscopic image by the plural models.

[Supplementary Note 7]

The image processing device according to Supplementary Note 1, wherein the inference means is configured to execute a first mode or a second mode while switching between the first mode and the second mode based on a predetermined condition, wherein, in the first mode, the inference means is configured to select a model with a best accuracy indicated by the predicted value from the plural models, and make the inference based on the selected model and the endoscopic image, and wherein, in the second mode, the inference means is configured to generate an inference result obtained by weighting, based on the predicted value, each inference result based on the endoscopic image by the plural models.

[Supplementary Note 8]

The image processing device according to Supplementary Note 7, wherein the inference means is configured to execute the first mode or the second mode while switching between the first mode and the second mode based on whether or not a presence or absence of detection of a disorder other than a target disorder of the lesion analysis.

[Supplementary Note 9]

The image processing device according to Supplementary Note 7, wherein the inference means is configured to execute the first mode or the second mode while switching between the first mode and the second mode based on an external input.

[Supplementary Note 10]

The image processing device according to Supplementary Note 1, wherein the inference means is configured to select a predetermined number of models with top accuracies indicated by the predicted value from the plural models, and generates an inference result obtained by weighting, based on the predicted value, each inference result by the predetermined number of models.

[Supplementary Note 11]

The image processing device according to Supplementary Note 1, wherein each of the plural model is a model obtained through a machine learning in which sets of the endoscopic image and correct answer data are used as training data, the correct answer data indicating an inference result to be outputted by the model when the endoscopic image is inputted to the model.

[Supplementary Note 12]

The image processing device according to Supplementary Note 1, further comprising

21 an output control means configured to output an inference result outputted by the inference means by a display device or an audio output device to support examiner's decision making.

[Supplementary Note 13]

An image processing method executed by a computer, the image processing method comprising:

acquiring a set value of a first index indicating an accuracy relating to a lesion analysis;

acquiring, for each of plural models which make inference regarding a lesion, a predicted value of a second index, which is an index of the accuracy other than the first index, on an assumption that the set value of the first index is satisfied; and making inference regarding the lesion included in an endoscopic image of an examination target, based on the predicted value of the second index and the plural models.

[Supplementary Note 14]

A storage medium storing a program executed by a computer, the program causing the computer to:

acquire a set value of a first index indicating an accuracy relating to a lesion analysis;

acquire, for each of plural models which make inference regarding a lesion, a predicted value of a second index, which is an index of the accuracy other than the first index, on an assumption that the set value of the first index is satisfied; and make inference regarding the lesion included in an endoscopic image of an examination target, based on the predicted value of the second index and the plural models.

While the invention has been particularly shown and described with reference to example embodiments thereof, the invention is not limited to these example embodiments. It will be understood by those of ordinary skilled in the art that various changes in form and details may be made therein without departing from the spirit and scope of the present invention as defined by the claims. In other words, it is needless to say that the present invention includes various modifications that could be made by a person skilled in the art according to the entire disclosure including the scope of the claims, and the technical philosophy. All patent and Non-Patent Literatures mentioned in this specification are incorporated by reference in its entirety.

DESCRIPTION OF REFERENCE NUMERALS 1, 1A, 1X Image processing device
2 Display device
3 Endoscope
4 Server device
11 Processor
12 Memory
13 Interface
14 Input unit
15 Light source unit
16 Audio Output Unit
100, 100A Endoscopic examination system

What is claimed is:

1. An image processing device comprising:
at least one memory configured to store instructions; and
at least one processor configured to execute the instructions to:
acquire a set value of a first index indicating an accuracy relating to a lesion analysis;

acquire, for each of plural models which infer a lesion, a predicted value of a second index, which is an index of the accuracy other than the first index, on an assumption that the set value of the first index is satisfied; and infer the lesion included in an endoscopic image of an examination target, based on the predicted value of the second index, the plural models, and a threshold value for the lesion associated with a combination of the set value of the first index and the predicted value of the second index.

2. The image processing device according to claim 1, is wherein the second index has a trade-off relation with the first index.

3. The image processing device according to claim 1, wherein a combination of the first index and the second index is a combination of sensitivity and a false positive rate or a combination of sensitivity and the precision.

4. The image processing device according to claim 1, wherein, for each of plural models, the at least one processor is further configured to execute the instructions to:
acquire correspondence information indicative of a correspondence relation between the first index and the second index, and
acquire, as the predicted value, a value of the second index corresponding to the set value according to the correspondence information.

5. The image processing device according to claim 4, wherein the correspondence information indicates an ROC curve, an LROC curve, an FROC curve, or a PR curve.

6. The image processing device according to claim 4, wherein curves of the plural models on two-dimensional coordinates with the first index and the second index as coordinate axes include intersecting points at which the curves intersect each other.

7. The image processing device according to claim 1, wherein the at least one processor is further configured to execute the instructions to:
select a model with a best accuracy indicated by the predicted value from the plural models, and
infer the lesion based on the selected model and the endoscopic image.

8. The image processing device according to claim 1, wherein the at least one processor is further configured to execute the instructions to:
generate an inference result obtained by weighting, based on the predicted value, each inference result based on the endoscopic image by the plural models.

9. The image processing device according to claim 1, wherein the at least one processor is further configured to execute the instructions to:
execute a first mode or a second mode while switching between the first mode and the second mode based on a predetermined condition,
wherein, in the first mode, the at least one processor is further configured to execute the instructions to:
select a model with a best accuracy indicated by the predicted value from the plural models, and
infer the lesion based on the selected model and the endoscopic image, and
wherein, in the second mode, the at least one processor is configured to execute the instructions to generate an inference result obtained by weighting, based on the predicted value, each inference result based on the endoscopic image by the plural models.

10. The image processing device according to claim 9, wherein the at least one processor is further configured to execute the instructions to:

execute the first mode or the second mode while switching between the first mode and the second mode based on whether or not a presence or absence of detection of a disorder other than a target disorder of the lesion analysis.

11. The image processing device according to claim 9, wherein the at least one processor is further configured to execute the instructions to:

execute the first mode or the second mode while switching between the first mode and the second mode based on an external input.

12. The image processing device according to claim 1, wherein the at least one processor is further configured to execute the instructions to:

select a predetermined number of models with top accuracies indicated by the predicted value from the plural models, and generates an inference result obtained by weighting, based on the predicted value, each inference result by the predetermined number of models.

13. The image processing device according to claim 1, wherein each of the plural model is a model obtained through a machine learning in which sets of the endoscopic image and correct answer data are used as training data, the correct answer data indicating an inference result to be outputted by the model when the endoscopic image is inputted to the model.

14. The image processing device according to claim 1, wherein the at least one processor is further configured to further execute the instructions to:

output an inference result by a display device or an audio output device to support examiner's decision making.

15. An image processing method executed by a computer, the image processing method comprising:

acquiring a set value of a first index indicating an accuracy relating to a lesion analysis;

acquiring, for each of plural models which infer a lesion, a predicted value of a second index, which is an index of the accuracy other than the first index, on an assumption that the set value of the first index is satisfied; and inferring the lesion included in an endoscopic image of an examination target, based on the predicted value of the second index, the plural models, and a threshold value for the lesion associated with a combination of the set value of the first index and the predicted value of the second index.

16. A non-transitory computer readable storage medium storing a program executed by a computer, the program causing the computer to:

acquire a set value of a first index indicating an accuracy relating to a lesion analysis;

acquire, for each of plural models which infer a lesion, a predicted value of a second index, which is an index of the accuracy other than the first index, on an assumption that the set value of the first index is satisfied; and infer the lesion included in an endoscopic image of an examination target, based on the predicted value of the second index, the plural models, and a threshold value for the lesion associated with a combination of the set value of the first index and the predicted value of the second index.

* * * * *